United States Patent
Scott et al.

[11] Patent Number: 5,898,088
[45] Date of Patent: Apr. 27, 1999

[54] PRODUCTION OF PENTAFLUOROETHANE

[75] Inventors: John David Scott, Northwich; Charles John Shields; Paul Nicholas Ewing, both of Warrington, all of United Kingdom

[73] Assignee: Imperial Chemical Industries PLC, London, United Kingdom

[21] Appl. No.: 08/663,068

[22] PCT Filed: Dec. 7, 1994

[86] PCT No.: PCT/GB94/02677

§ 371 Date: Jun. 14, 1996

§ 102(e) Date: Jun. 14, 1996

[87] PCT Pub. No.: WO95/16654

PCT Pub. Date: Jun. 22, 1995

[30] Foreign Application Priority Data

Dec. 16, 1993 [GB] United Kingdom ................. 932576

[51] Int. Cl.[6] .................... C07C 19/08; C07C 17/20; C07C 17/093; B01J 27/06

[52] U.S. Cl. ................. 570/166; 570/165; 570/168; 570/169

[58] Field of Search .................. 570/165, 166, 570/168, 169

[56] References Cited

U.S. PATENT DOCUMENTS

| 5,155,082 | 10/1992 | Tung et al. | 502/228 |
| 5,494,876 | 2/1996 | Tsuji et al. | 502/224 |
| 5,494,877 | 2/1996 | Tsuji et al. | 502/228 |

FOREIGN PATENT DOCUMENTS

| 0 456 552 | 11/1991 | European Pat. Off. |
| 901 297 | 7/1962 | United Kingdom . |
| WO 92/19576 | 11/1992 | WIPO . |

*Primary Examiner*—Alan L. Rotman

[57] ABSTRACT

A process for the production of pentafluoroethane which comprises the steps (i) producing a composition comprising a compound of formula $C_2HCl_xF_y$ in which x=1, 2 or 3 and y=2, 3 or 4 provided that x+y is 5, contaminated with a compound of formula $C_2Cl_{x+1}F_y$, (ii) separating the compound of formula $C_2HCl_xF_y$ from the compound of formula $C_2Cl_{x+1}F_y$ and (iii) contacting the compound of formula $C_2HCl_xF_y$ with hydrogen fluoride in the presence of a fluorination catalyst whereby to produce pentafluoroethane.

18 Claims, 7 Drawing Sheets

PRODUCTION OF PENTAFLUOROETHANE

CROSS REFERENCE

This application is a 371 of PCT/GB 94/02677 filed Dec. 7, 1994.

This invention relates to a process for the production of pentafluoroethane.

Pentafluoroethane (HFA 125) has been proposed as a component of non ozone-depleting refrigerant blends, for example as a component of blends together with other hydrofluoroalkanes such as difluoromethane HFA 32, 1,1,1-trifluoroethane HFA 143a, and/or 1,1,1,2-tetrafluoroethane HFA 134a, which are suitable replacements for various chlorofluorocarbons and hydrochlorofluorocarbons and in particular the refrigerant blend R502 and chlorodifluoromethane HCFC 22 in the many applications in which chlorofluorocarbons and hydrochlorofluorocarbons are employed, and in particular in low-temperature refrigeration.

Recently, many processes have been proposed for the production of pentafluoroethane, amongst which may be mentioned the hydrogenation of chloropentafluoroethane CFC 115 and the hydrofluorination of perchloroethylene.

The hydrogenation of chloropentafluoroethane is typically effected under conditions which provide incomplete conversion of chloropentafluoroethane and which therefore result in the production of pentafluoroethane contaminated with chloropentafluoroethane. Chloropentafluoroethane and pentafluoroethane have very similar boiling points, $-38°$ C. and $-48°$ C. respectively, and also form a minimum boiling azeotrope, and are difficult to separate by conventional techniques such as distillation with the result that the pentafluoroethane produced may have an unacceptably low purity due to the presence of significant amounts of CFC 115, for example an amount of CFC 115 which may be as much as 5 wt %.

The hydrofluorination of perchloroethylene has a serious productivity restriction due to the large number of halogen exchange reactions which are required in order to yield pentafluoroethane. Moreover, the catalysts which are typically employed in the hydrofluorination of perchloroethylene become seriously coked and consequently deactivated by the sequential halogen exchange reactions which occur.

Furthermore, in addition to the sequential halogen exchange reactions through tetrachlorofluoroethane HCFC 121, trichlorodifluoroethane HCFC 122, dichlorotrifluoroethane HCFC 123 and chlorotetrafluoroethane HCFC 124 which lead to the production of pentafluoroethane, the sequential reactions through pentachlorofluoroethane CFC 111, tetrachlorodifluoroethane CFC 112, trichlorotrifluoroethanes (CFCs 113 and 113a) and dichlorotetrafluoroethanes (CFCs 114 and 114a) which lead to the production of chloropentafluoroethane may, under certain conditions and with certain catalysts, leading to contamination of pentafluoroethane with significant amounts of chloropentafluoroethane.

Recently much attention has focused on achieving a satisfactory separation of chloropentafluoroethane from pentafluoroethane. Thus, for example a variety of processes for the purification of pentafluoroethane have been disclosed in U.S. Pat. No. 5,087,329, WO94/22793, WO93/23355, JP6-92879, WO94/20441, WO94/19301 and EP 0 612 709, all of which focus on the removal of chloropentafluoroethane from pentafluoroethane.

In contrast, we have now devised a process for the production of pentafluoroethane in which the production of chloropentafluoroethane may be substantially reduced or even eliminated, thus reducing or even completely overcoming the problem of separation of chloropentafluoroethane from pentafluoroethane.

According to the present invention there is provided a process for the production of pentafluoroethane which comprises the steps (i) producing a composition comprising a compound of formula $C_2HCl_xF_y$ in which x=1, 2 or 3 and y=2, 3 or 4 provided that x+y is 5, contaminated with a compound of formula $C_2Cl_{x+1}F_y$ in which x and y have the meanings above, (ii) separating the compound of formula $C_2HCl_xF_y$ from the compound of formula $C_2Cl_{x+1}F_y$ and (iii) contacting the compound of formula $C_2HCl_xF_y$ with hydrogen fluoride in the presence of a fluorination catalyst whereby to produce pentafluoroethane.

Whilst in many embodiments of the invention steps (i), (ii) and (iii) are effected in that order, this is not necessarily the case in order to obtain pentafluoroethane containing low levels (as hereinafter described) of chloropentafluoroethane and steps (i), (ii) and (iii) may be effected in a different order, for example step (ii) may be effected after steps (i) and (iii), particularly where step (iii) is operated under conditions such that the conversion of compounds of formula $C_2Cl_{x+1}F_y$ to chloropentafluoroethane are low, say less than 50%, and preferably less than 25%.

In step (i) of the process the composition may be produced by the chlorination and/or hydrofluorination of a haloethene, for example perchloroethylene, trifluoroethylene, chlorodifluoroethylene or dichlorofluoroethylene or of a hydrohaloethane, for example a tetrafluoroethane or chlorotrifluoroethane.

In alternative preferred embodiments ((A) and (B)) of the invention (described in more detail hereinafter), step (i) of the process comprises either (A) chlorinating trichloroethylene or a compound of formula $C_2H_2X_4$ wherein X is fluorine or chlorine, for example a tetrachloroethane, tetrafluoroethane or chlorotrifluoroethane, or (B) contacting a perhaloethylene or pentahaloethane with hydrogen fluoride in the liquid or the vapour phase and in the presence of a fluorination catalyst.

The process is advantageously operated as a continuous process in which the product stream from step (iii) is treated, conveniently by distillation, to separate unconverted compounds of formula $C_2HCl_xF_y$ from pentafluoroethane and recycling unconverted compounds of formula $C_2HCl_xF_y$ to step (i) or step (iii), and preferably to step (i). Furthermore, the product stream from step (iii) may contain compounds of formula $C_2Cl_{x+1}F_y$ and in this case, we prefer that the recycle stream comprises less than 15 wt %, more preferably less than 10 wt % and especially less than 5 wt %, of compounds of formula $C_2Cl_{x+1}F_y$ based on the total weight of compounds of formula $C_2HCl_xF_y$ and $C_2Cl_{x+1}F_y$ present in the recycle stream.

The composition formed in step (i) of the process of the present invention may be a single compound of formula $C_2HCl_xF_y$ contaminated with a single compound of formula $C_2Cl_{x+1}F_y$, for example chlorotetrafluoroethane contaminated with dichlorotetrafluoroethane, dichlorotrifluoroethane contaminated with trichlorotrifluoroethane or trichlorodifluoroethane contaminated with tetrachlorodifluoroethane. Usually the starting composition will comprise a composition of two or more and even a composition comprising all of the compounds of formula $C_2HCl_xF_y$ contaminated with two or more and even all of the compounds of formula $C_2Cl_{x+1}F_y$, especially where the composition is produced by one of the alternative preferred embodiments (A) or (B) in step (i) of the process. However, the composition will usually comprise at least chlorotetrafluoroethane and dichlorotetrafluoroethane, and it is the separation of dichlorotetrafluoroethane from chlorotetrafluoroethane which is especially preferably effected in step (ii) of the process.

The product composition of step (i) of the process typically comprises from about 0.1% to about 20%, and more typically from about 0.5% to about 15%, by weight of compounds of formula $C_2Cl_{x+1}F_y$ as a percentage of the total weight of compounds of formula $C_2Cl_{x+1}F_y$ and compounds of formula $C_2HCl_xF_y$ produced. We prefer that the process of step (i) is effected such that the product composition formed in step (i) comprises from about 0.5% to about 10% by weight compounds of formula $C_2Cl_{x+1}F_y$ as a percentage of the total weight of compounds of formula $C_2Cl_{x+1}F_y$ and compounds of formula $C_2HCl_xF_y$ produced. The product composition from step (i) also comprises unconverted starting materials, by-product hydrogen chloride and small amounts of other by-products depending upon the particular process employed in step (i).

Substantial advantage is gained by the process of the invention since effective separation of compounds of formula $C_2Cl_{x+1}F_y$ and in particular dichlorotetrafluoroethanes (CFCs 114 and 114a, boiling point 3.3° C.±0.3° C. depending upon the isomer) and trichlorotrifluoroethanes (CFCs 113 and 113a, boiling point 46.6° C.±1.0° C. depending upon the isomer) from compounds of formula $C_2HCl_xF_y$ and in particular chlorotetrafluoroethanes (HCFCs 124, and 124a, boiling point −11.0° C.±1.0° C. depending upon the isomer) and dichlorotrifluoroethanes (HCFCs 123, 123a and 123b, boiling point 27.5° C.±1.0° C. depending upon the isomer) may be performed using conventions techniques, and preferably by distillation. The separation step (ii) is preferably carried out so that at least 50 wt %, more preferably at least 75 wt % and especially at least 90 wt %, of the compounds of formula $C_2Cl_{x+1}F_y$ present in the composition produced in step (i) are separated from the compounds of formula $C_2HCl_xF_y$.

Thus the process of the invention removes, or at least substantially reduces the chlorofluorocarbon(s) from which chloropentafluoroethane would be produced prior to the reaction step in which chloropentafluoroethane would otherwise be produced. The separation step (ii) may be effected such that the compounds of formula $C_2HCl_xF_y$ recovered from the separation and fed to step (iii) of the process contains less than 10%, preferably less than 5%, more preferably less than 2% and especially less than 1%, by weight of compounds of formula $C_2Cl_{x+1}F_y$. In embodiments of the invention in which step (i) of the process comprises one of the preferred embodiments (A) or (B) for step (i), and in particular where step (i) comprises preferred embodiment (B), or the chlorination of 1,1,1,2-tetrafluoroethane, then the essential separation to be performed is separating dichlorotetrafluoroethane from chlorotetrafluoroethane, and the chlorotetrafluoroethane recovered from the separation and fed to step (iii) of the process preferably contains less than 2% by weight dichlorotetrafluoroethane and more preferably less than 1.0%, especially less than 0.5% dichlorotetrafluoroethane. As a result of the effective separation of CFCs, especially trichlorotrifluoroethanes and diclorotetrafluoroethanes, from the process prior to the formation of substantial quantities of chloropentafluoroethane, the level of chloropentafluoroethane in the pentafluoroethane produced by the process of the invention and prior to any specific purification step performed specifically to remove chloropentafluoroethane from pentafluoroethane, may be as low as less than 5 wt %, preferably less than 3 wt %, more preferably less than 2 wt % and especially less than 1 wt % chloropentafluoroethane based on the total weight of chloropentafluoroethane and pentafluoroethane produced.

In preferred embodiment (A) of the invention in which step (i) comprises the chlorination of trichloroethylene or a compound of formula $C_2H_2X_4$ wherein X is fluorine or chlorine, we prefer that the starting material is a tetrachloroethane, tetrafluoroethane or chlorotrifluoroethane, and especially that the starting material is 1,1,1,2-tetrafluoroethane.

Chlorination techniques are well known in the art and any such chlorination technique may be employed in step (i) of the process. Thus, the chlorination may be effected in the liquid or vapour phase and the chlorination may be photochemically, catalytically or thermally activated.

Where the starting material is 1,1,1,2-tetrafluoroethane, the chlorination is preferably effected with a molar ratio of 1,1,1,2-tetrafluoroethane to chlorine in the range from about 10:1 to about 1:1, more preferably in the range from about 6:1 to about 1:1 and especially in the range from about 5:1 to about 2:1 in order to reduce the amount of dichlorotetrafluoroethane produced.

The chlorination step (i) and the hydrofluorination step (iii) may be performed in the same reaction vessel, in which case the process is a chlorofluorination, the product stream from the reactor being treated, for example by distillation, to separate one or more recycle streams comprising compounds of formula $C_2HCl_xF_y$ and unreacted starting compounds of formula $C_2H_2X_4$, from a pentafluoroethane stream for recovery, and a waste stream comprising compounds of formula $C_2Cl_{x+1}F_y$. Suitable conditions of temperature and pressure etc. for the chlorofluorination of 1,1,1,2-tetrafluoroethane are well known in the art and are described, for example in U.S. Pat. No. 5,258,561, although we prefer to employ chlorine and 1,1,1,2-tetrafluoroethane in the ratios given hereinabove rather than those given in the aforementioned US Patent.

Alternatively in preferred embodiment (A) of the invention, steps (i) and (iii) may be performed in separate reaction vessels, and the step (i) chlorination reaction vessel and the step (iii) hydrofluorination vessel are preferably arranged in series or in parallel.

In the series reactor arrangement, tetrafluoroethane is chlorinated in the vapour phase in the step (i) reaction vessel and the product stream is fed to a separation system in which hydrogen chloride is taken out, for example using aqueous scrubbers or distillation, and unconverted tetrafluoroethane is separated, for example by distillation, and recycled to the chlorination reactor vessel, leaving a stream comprising the chlorotetrafluoroethane and dichlorotetrafluoroethane products. The chlorotetrafluoroethane/dichlorotetrafluoroethane mixture is fed to a distillation operation in which the chlorotetrafluoroethane is separated from the dichlorotetrafluoroethane and the chlorotetrafluoroethane is then fed to the step (iii) hydrofluorination reaction vessel containing a fluorination catalyst.

In a parallel reactor arrangement, the chlorination and hydrofluorination reaction vessels are arranged in parallel and the product streams from each vessel may be combined and/or fed to a common purification system, for example a series of distillation operations in which pentafluoroethane, tetrafluoroethane, chlorotetrafluoroethane and dichlorotetrafluoroethane are separated from each other, chlorotetrafluoroethane is recycled to the hydrofluorination reactor and tetrafluoroethane is recycled to the chlorination reactor. In this parallel operation, we prefer that the process stream from the hydrofluorination reactor is first treated, for example by phase separation and distillation, in order to remove and recycle a major proportion of unreacted hydrogen fluoride prior to being combined with the product stream from the chlorination reactor.

In the second preferred embodiment (B) of the invention in which step (i) comprises contacting a perhaloethylene or pentahaloethane with hydrogen fluoride in the liquid or vapour phase and in the presence of a fluorination catalyst, we prefer that the starting compound is perchloroethylene, and we also prefer that the process is effected in the vapour phase at an elevated temperature.

The temperature at which step (i) is effected may be in the range from about 150° C. to about 400° C., preferably from about 180° C. to about 380° C. and especially from about 200° C. to about 370° C. Atmospheric, subatmospheric or superatmospheric pressures may be employed, although to aid throughput of vapours through the equipment we prefer to employ superatmospheric pressure, say a superatmospheric pressure up to about 30 barg, and particularly a pressure in the range from about 5 barg to about 20 barg.

The relative proportion of hydrogen fluoride to perchloroethylene may vary within wide limits although we generally prefer to employ a stoichiometric molar excess of hydrogen fluoride. The molar ratio of hydrogen fluoride to perchloroethylene will usually be greater than about 3:1 and preferably is greater than 5:1. We prefer to employ a molar ratio of hydrogen fluoride to perchloroethylene in the range from about 5:1 to about 20:1 and preferably in the range from about 7:1 to about 15:1, especially in the range from about 7:1 to about 12:1.

The catalyst employed in step (i) of this preferred embodiment (B) of the process may be any known fluorination catalyst, and in particular any fluorination catalyst which has a high activity for the conversion of perchloroethylene to hydrochlorofluoroethanes, for example catalysts based upon chromia, chromium oxyfluoride, alumina or aluminium fluoride and which may also comprise one or more metals, for example nickel, cobalt, iron, zinc etc. We particularly prefer to employ a chromia or zinc carried on chromia catalyst in step (i) since this catalyst has a particularly high per pass conversion of perchloroethylene to hydrochlorofluoroethanes.

In this preferred embodiment (B) of the invention in which step (i) comprises hydrofluorination, both steps (i) and (iii) are hydrofluorination processes and the catalyst employed in steps (i) and (iii) may be the same or different so that the two steps (i) and (iii) may be affected, if desired, in a single reaction vessel over a single catalyst bed comprising a fluorination catalyst whereby to produce pentafluoroethane. In this case the product stream from the single reactor may be fed to a purification system for example a series of distillation columns, to separate one or more recycle streams comprising compounds of formula $C_2HCl_xF_y$, and unreacted starting compound, for example perchloroethylene, from a pentafluoroethane stream for recovery, and a waste stream comprising compounds of formula $C_2Cl_{x+1}F_y$. In this single reactor embodiment, the catalyst may be a catalyst as described for step (i) or step (iii), as desired.

However, in this preferred embodiment (B) of the invention we have further found that different catalysts may, in some cases, be preferable for steps (i) and (iii) of the process. Thus, it may be preferred to employ a catalyst having a high activity (per pass conversion) for the conversion of perchloroethylene in step (i) of the process whilst it is preferred to employ a catalyst which demonstrates a high selectivity for the production of pentafluoroethane from the hydrochlorofluoroethanes in step (iii).

The catalysts for step (i) and (iii) of the process may be present in different reaction zones of the same reactor vessel or they may each be carried in a separate reactor vessel.

Where the catalyst for step (i) and the catalyst for step (iii) are carried in separate reaction vessels, then the two reaction vessels (hereafter "reactors") may be arranged in parallel or in series.

In embodiments in which the step (i) and step (iii) reactors are arranged in series, the product stream from one of the step (i) or (iii) reaction vessels is passed to the other vessel and the product steam of this other reaction vessel is fed to a purification system in which step (ii) is effected. Thus, the product stream from the step (i) reactor may be passed to the step (iii) reactor and the product steam from the step (iii) reactor may be fed to a purification system in which step (ii) is effected. Alternatively, the product stream from the step (i) reactor may be passed to the purification system in which step (ii) is effected and one or more streams from the purification system comprising unreacted starting materials and compounds of formula $C_2HCl_xF_y$ from which compounds of formula $C_2Cl_{x+1}F_y$ have been separated may be passed to the step (iii) reactor. The product stream from the step (iii) reactor may be passed to the step (i) reactor.

However, it is also preferable that hydrogen chloride is substantially removed before step (iii) of the process. Hydrogen chloride is produced as a substantial by-product from step (i) of the process and we prefer therefore that from the product stream from the step (i) reactor is fed to the purification system in which step (ii) is effected and the product stream from the step (iii) reactor is passed to the step (i) reactor.

According to a further preferred embodiment of the invention there is provided a process for the production of pentafluoroethane which comprises (i) contacting perchloroethylene with hydrogen fluoride in the presence of a fluorination catalyst to produce a composition comprising a compound of formula $C_2HCl_xF_y$ in which x=1, 2 or 3 and y=2, 3 or 4 provided that x+y is 5, contaminated with a compound of formula $C_2Cl_{x+1}F_y$ in which x and y have the meanings above, (ii) separating the compound of formula $C_2HCl_xF_y$ from the compound of formula $C_2Cl_{x+1}F_y$ and (iii) contacting the compound of formula $C_2HCl_xF_y$ with hydrogen fluoride in the presence of a fluorination catalyst whereby to produce pentafluoroethane and wherein the product stream from step (iii) of the process is recycled to the step (i) reactor.

In embodiments in which the step (i) and step (iii) reaction vessels are arranged in parallel, the product streams from the reactors are preferably fed to a common purification system in which step (ii) is effected and from which pentafluoroethane is recovered, unconverted perhaloethylene is recycled to the step (i) reaction vessel and unconverted compounds of formula $C_2HCl_xF_y$ are recycled to the step (iii) reaction vessel.

In step (ii) the stream fed to the purification system from the reactor in a single reactor embodiment or from either of the two reactors in a two-reactor embodiment typically comprises compounds of formula $C_2HCl_xF_y$, in particular dichlorotrifluoroethanes and chlorotetrafluoroethanes, compounds of formula $C_2Cl_{x+1}F_y$, in particular trichlorotrifluoroethanes and dichlorotetrafluoroethanes, pentafluoroethane, chloropentafluoroethane, unreacted hydrogen fluoride and perchloroethylene, by-product hydrogen chloride and small amounts of other by-products, for example, 1,1,1-trifluoro-2-chloroethane and 1,1,1,2-tetrafluoroethane.

This stream may be fed, for example, to a purification system which comprises a first distillation column from which hydrogen fluoride, dichlorotrifluoroethane [HCFC 123/123a] and other heavies are removed as a bottom fraction whilst the remainder of the stream is removed as a top fraction. The bottom fraction from this first column may be recycled to the reactor or to one or both of the reactors.

The top fraction from the first column, after aqueous scrubbing and drying if desired in order to remove the acid components, hydrogen chloride and hydrogen fluoride, may be fed to a second distillation column from which pentafluoroethane [HFA 125] is withdrawn together with chloropentafluoroethane [CFC 115] as a top fraction whilst the remainder of the stream, comprising mainly chlorotetrafluoroethane [HCFC 124/124a], chlorotrifluoroethane [HCFC 133/133a], tetrafluoroethane [HFA 134/134a] and dichlorotetrafluoroethane [CFC 114/114a] is withdrawn as a bottom fraction. The pentafluoroethane containing chloropentafluoroethane withdrawn as a top fraction may be further treated to effect purification of the pentafluoroethane.

The bottom fraction from the second column may be fed to a third distillation column from which tetrafluoroethane [HFA 134/134a] is withdrawn as a top fraction whist the remainder of the stream is withdrawn as a bottom fraction and passed to a fourth distillation column from which chlorotetrafluoroethane [HCFC 124/124a] is withdrawn as a top fraction whilst dichlorotetrafluoroethane [CFC 114/114a] and chlorotrifluoroethane [HCFC 133/133a] are withdrawn as a bottom fraction. The chlorotetrafluorethane [HCFC 124/124a] may be recycled to a reactor for fluorination to pentafluoroethane [HFA 125]. The bottom fraction from the fourth column is usually disposed of, for instance by thermal oxidation.

The purification system employed in the preferred embodiment (B) of the invention preferably comprises a first distillation column in which unreacted perhaloethylene and unconverted compounds of formula $C_2HCl_xF_y$ in which x is 1, 2 or 3, are separated (as a bottoms stream) from the other components (as a tops stream) and recycled to the step (i) reactor, and at least one further distillation column by which pentafluoroethane is separated from the other components of the tops stream and recovered and chlorotetrafluoroethane is separated from dichlorotetrafluoroethane and recycled.

The tops stream from the first distillation column is preferably treated in order to remove at least hydrogen chloride. In particular the tops steam from the first distillation column may be scrubbed with water to remove hydrogen fluoride and hydrogen chloride before being fed to the at least one further distillation column. However, in is case the hydrogen fluoride in the tops stream is also removed, resulting in a lower hydrogen fluoride efficiency for the process. Alternatively, the tops stream from the first distillation column may itself be distilled in order to separate a tops stream comprising hydrogen chloride, pentafluoroethane and chloropentafluoroethane from a bottoms stream comprising the other components. This bottoms stream may then be fed to the at least one further distillation column, whilst the tops stream may be fed to a distillation column in order to recover pentafluoroethane from the tops stream.

Where aqueous scrubbing is employed to remove hydrogen chloride and hydrogen fluoride, the at least one further distillation column preferably comprises two distillation columns in which in the first further column pentafluoroethane is separated from chlorotetrafluoroethane and dichlorotetrafluoroethane and in the second column dichlorotetrafluoroethane is separated from chlorotetrafluoroethane. Where distillation is employed to separate hydrogen chloride from the tops stream from the first distillation column, the at least one further distillation column need only comprise one distillation column in which chlorotetrafluoroethane is separated from dichlorotetrafluoroethane. Where this option (i.e. distillation to remove hydrogen chloride) is employed, then the distillation of 114/114a from 124/124a is effected in the presence of hydrogen fluoride, and the tops stream from the column in which this separation is effected, is a novel composition comprising chlorotetrafluoroethane, dichlorotetrafluoroethane and hydrogen fluoride which is particularly suitable for hydrofluorination to pentafluoroethane, i.e. as in step (iii) of the process of the present invention.

According to a second aspect of the invention there is provided a composition suitable for conversion to pentafluoroethane which comprises: (i) from at least 50% by weight to about 95% by weight chlorotetrafluoroethanes, (ii) from about 0.5% to about 20% by weight hydrogen fluoride and (iii) less than 2% by weight dichlorotetrafluoroethanes, wherein % by weight re calculated based on the total weight of these three components present in the composition.

The composition may also comprise small amounts, not usually grater than 10% by weight of the composition, and typically not greater than 5% by weight of the composition of other components, for example other compounds of formula $C_2HCl_xF_y$ and other compounds of formula $C_2Cl_{x+1}F_y$. Consequently the above % by weight for the components of the composition will also be usually % by weight of the tote weight of the composition. Preferably, the amount of dichlorotetrafluoroethanes in the composition will be less than 1 wt %, especially less than 0.5 wt %. The composition preferably also comprises from about 1 wt % to about 10 wt % hydrogen fluoride and will usually comprise at least 75 wt % chlorotetrafluoroethanes.

Step (iii) of the process may be carried out in the liquid or vapour phase, although we prefer vapour phase operation, particularly where step (i) comprises the vapour phase hydrofluorination of a perhaloethylene or pentahaloethane. The vapour phase reaction of dichlorotrifluoroethane and chlorotetrafluoroethane with hydrogen fluoride is well known in the art and suitable conditions of temperature and pressure, suitable fluorination catalysts and relative proportions of reactants have been well documented.

Suitable fluorination catalysts include those based upon chromia and chromium oxyfluoride or alumina and aluminium fluoride. Activity promoting amounts of other metals, for example zinc, nickel and iron may also be present. We particularly prefer to employ a catalyst as described in EP 502605 or WO 93/16798, and especially a catalyst as described in EP 502605 which may comprise an activity promoting amount of zinc carried on chromia or chromium oxyfluoride.

The temperature in step (iii) of the process may be in the range from about 200° C. to about 500° C., preferably from about 250° C. to about 350° C. The process is conveniently carried out at about atmospheric pressure although subatmospheric or superatmospheric pressures, say up to about 20 bar, may be employed if desired. Indeed superatmospheric pressures from about 2 to about 15 bar are generally employed in order to aid throughput of the gases and reduce the size of the reactors required. [In embodiments of the preferred embodiment of the invention (B) in which two reaction vessels are employed, we generally prefer that the reactors are operated at substantially the same pressure, any difference in pressure between the vessels being the natural result only of the flow of gases through the equipment.]

The molar ratio of hydrogen fluoride to chlorotetrafluoroethane may be in the range from about 1 to about 10; preferably a molar excess of hydrogen fluoride is employed.

The invention will now be described but not limited with reference to the drawings in which.

Figure 1:
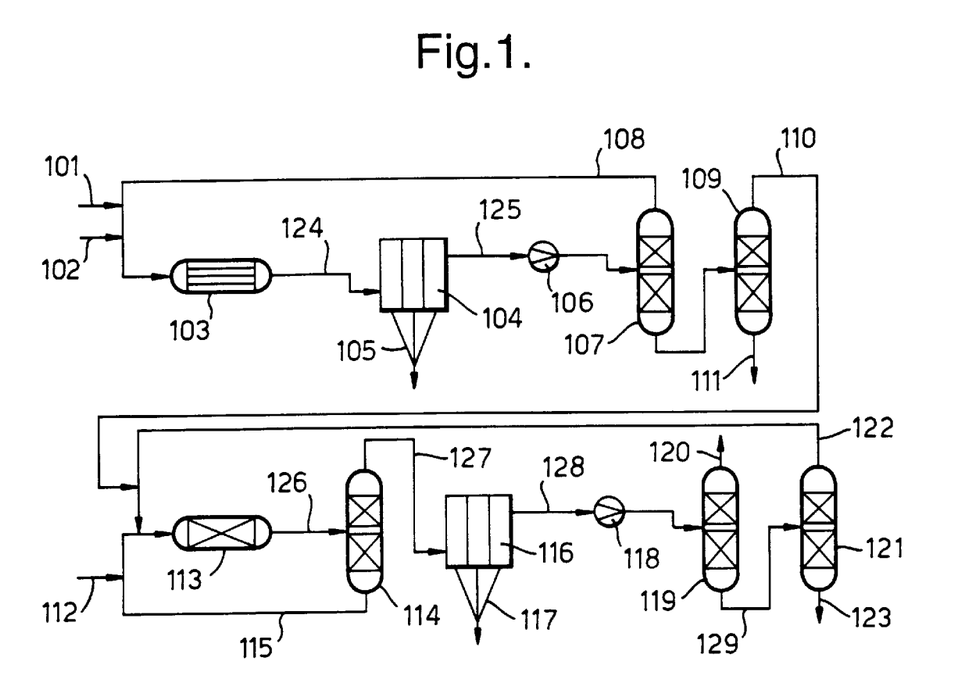
FIG. 1 is a schematic flow diagram of an embodiment of the invention using two reactors in which step (i) is the chlorination of 1,1,1,2-tetrafluoroethane and the reactors are arranged in series.

With reference to FIG. 1, a gaseous chlorine feed stream 101, and gaseous 1,1,1,2-tetrafluoroethane feed steam 102 are fed to a chlorination reactor vessel 103. The product gas stream 124 from the chlorination reactor is fed to an aqueous scrubber system 104 in which hydrogen chloride and unreacted chlorine are separated as in aqueous stream 105 from an organic stream 125. The organic stream 125 is dried and compressed in compressor 106 before being fed to a distillation column 107 in which 1,1,1,2-tetrafluoroethane (HFA 134a) is separated from chlorotetrafluoroethane (HCFC 124) and dichlorotetrafluoroethane (CFC 114a). The HFA 134a stream 108 is recycled to the chlorination reactor vessel 103. The HCFC124/CFC 114a stream is fed to a distillation column 109 in which a HCFC 124 stream 110 is separated from a CFC 114a stream 111. The HCFC 124 product stream 110 from the distillation column is then fed together with gaseous hydrogen fluoride 112 to a hydrofluorination reactor 113 containing chromia catalyst. The product gas stream 126 from this reactor is fed to a distillation column 114 in which a stream 115 comprising unreacted hydrogen fluoride and HCFC 124 are separated from other components of the product stream and recycled to the reactor 113. The remainder of the product stream 127 from the distillation column is fed to an aqueous scrubber system 116 in which hydrogen chloride and any remaining hydrogen fluoride are separated as an aqueous stream 117 from an organic stream 128. The organic stream 128 is fed to a compressor 118 and then fed to a distillation column 119 in which a pentafluoroethane product stream 120 is separated from a stream 129 comprising the other organics. The organic stream 129 is then fed to a second distillation column 121 in which a HCFC 124 stream 122 is separated from a heavy by-product stream 123. The HCFC 124 stream 122 is recycled to the reactor 13.

Figure 2:
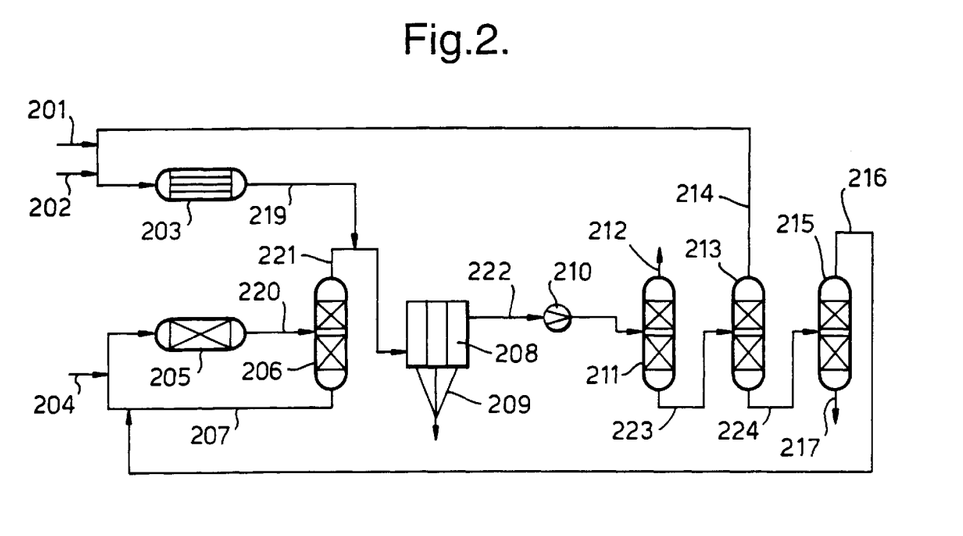
FIG. 2 is a schematic flow diagram of an embodiment of the invention using two reactors in which step (i) is the chlorination of 1,1,1,2-tetrafluoroethane and the reactors are arranged in parallel.

In the embodiment of FIG. 2, a gaseous chlorine feed stream 201, and gaseous 1,1,1,2-tetrafluoroethane feed stream 202 are fed to a chlorination reactor vessel 203 comprising an Inconel tube.

A hydrogen fluoride stream 204 and the HCFC 124 recycle stream 216 from a distillation column 215 (as described hereafter) are fed to a hydrofluorination reactor 205 containing chromia catalyst and the product gas stream 220 is fed to a distillation column 206 in which a stream 207 comprising unreacted hydrogen fluoride and HCFC 124 are separated from a stream 221 comprising the remainder of the product stream and the stream 207 is recycled to the reactor 205. The stream 221 from the distillation column 206 is combined with the product stream 219 from the chlorination reactor 203 and fed to an aqueous scrubber system 208 in which hydrogen chloride, chlorine and any remaining hydrogen fluoride are separated as an aqueous stream 209 from an organic stream 222. The organic stream 222 from 208 is dried, compressed in compressor 210 and fed to a distillation column 211 to separate a pentafluoroethane stream 212 from an organic stream 223 comprising HFA 134a, HCFC 124 and CFC 114a. The organic stream 223 is fed to a distillation column 213 in which a HFA 134a stream 214 is separated from a stream 224 comprising HCFC 124 and CFC 114a. The HFA 134a stream 214 is recycled to the reactor 203. Stream 224 is fed to a distillation column 215 in which a HCFC 224 stream 216 is separated from a CFC 114a stream 217, and the HCFC 124 stream 216 is recycled to the reactor 205.

Figure 3:
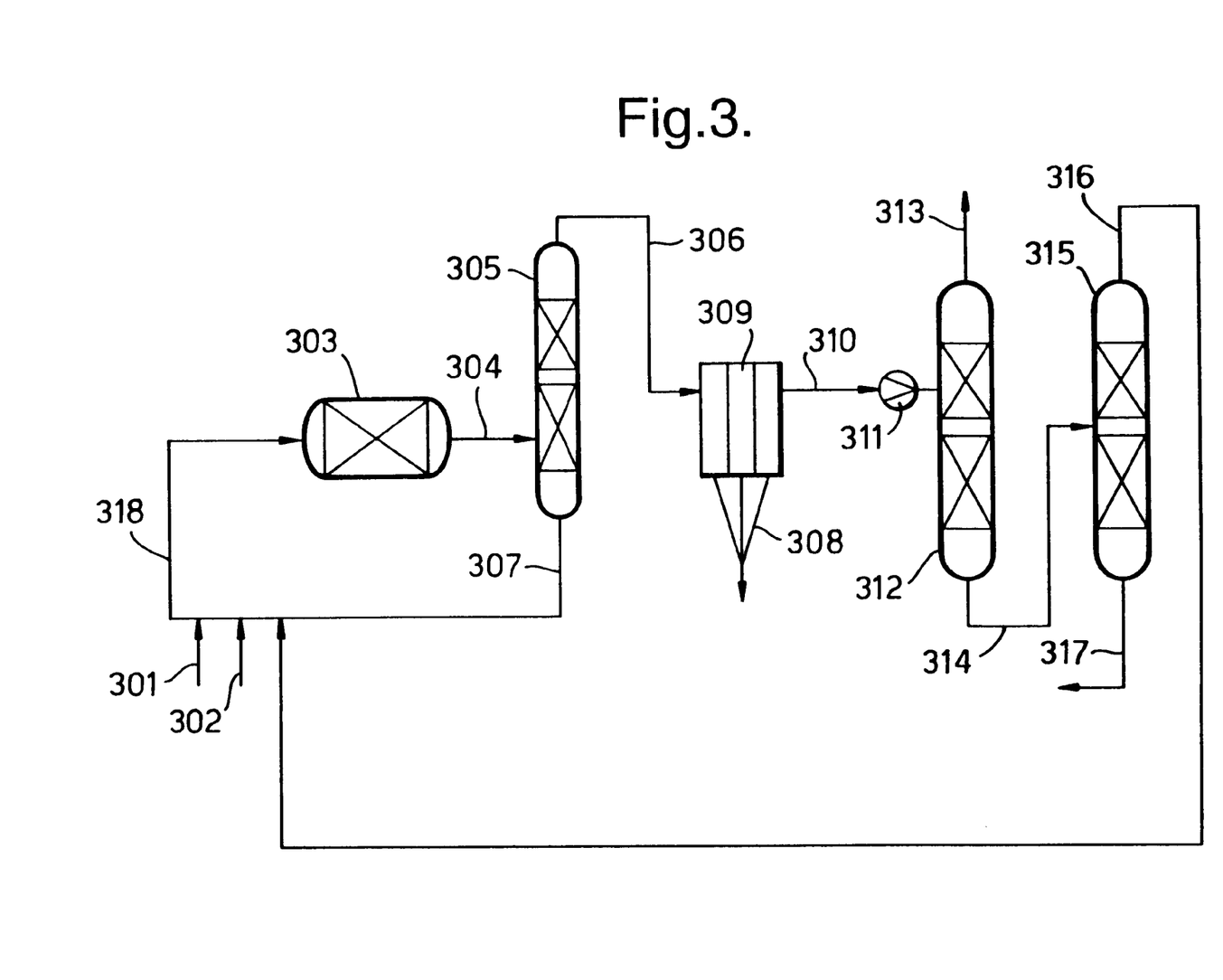
FIG. 3 is a schematic flow diagram of an embodiment of the invention in which step (i) is the hydrofluorination of perchloroethylene and steps (i) and (iii) are effected in a single reactor, and aqueous scrubbing is employed to remove hydrogen chloride.

In the embodiment of FIG. 3, a gaseous feed stream 318 comprising a feed hydrogen fluoride stream 301, a feed perchloroethylene stream 302, recycled hydrogen fluoride and organics stream (described hereinafter) 307 and a HCFC-124 recycle stream 316 is fed to a hydrofluorination reactor 303, containing chromia catalyst. The product gas stream 304 is fed to a distillation column 305 in which a stream 307 containing unreacted hydrogen fluoride, perchloroethylene and underfluorinated organic intermediates e.g. HCFCs 121, 122 and 123 is separated from a stream 306 comprising product HFA 125, HCFC 124, CFC 114/114a, HCl and HF. Stream 306 is fed to an aqueous scrubber system 309 in which hydrogen chloride and any remaining HF are separated as an aqueous stream 308 from an organic stream 310. The organics stream 310 is dried, compressed in compressor 311 and fed to a distillation column 312 to separate a HFA 125 stream 313 from stream 314 containing HCFC 124 and CFC 114/114a. Stream 314 is fed to a distillation column 315 in which a HCFC 124 stream 316 is separated from stream 317 enriched in CFC 114/114a.

Figure 4:
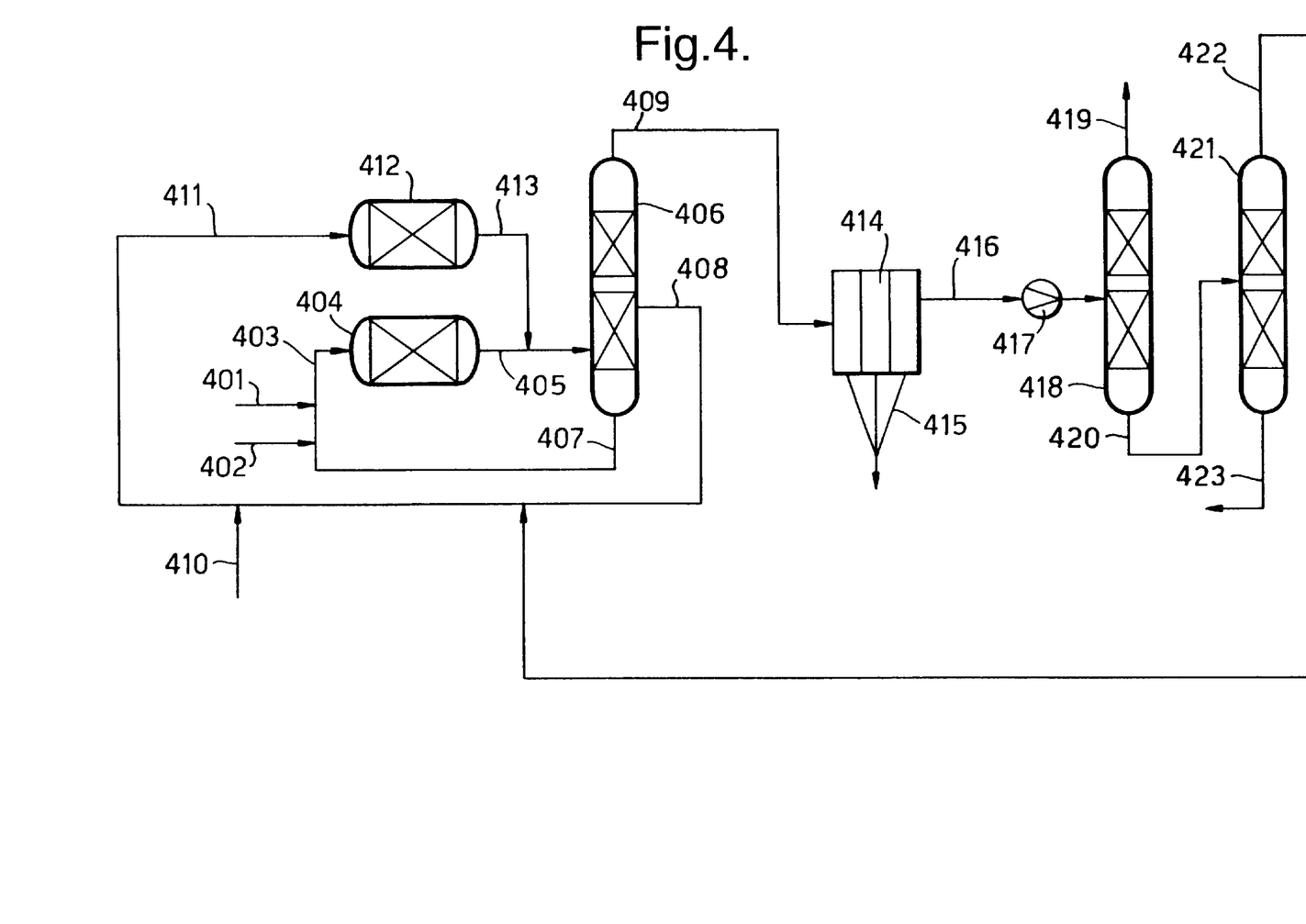
FIG. 4 is a schematic flow diagram of an embodiment of the invention using two reactors in which step (i) is the hydrofluorination of perchloroethylene and the reactors are arranged in parallel.

In the embodiment of FIG. 4, a gaseous stream 403 comprising feed hydrogen fluoride 401, feed perchloroethylene 402 and recycled hydrogen fluoride, perchloroethylene and underfluorinated intermediates to HFA 125 407, is fed to a hydrofluorination reactor 404 containing chromia catalyst. The product gas stream 405 is mixed with stream 413 containing product gas from a parallel hydrofluorination reactor 412 and fed to a distillation column 406 in which a stream 407 containing HF and perchloroethylene (and some underfluorinated HCFCs 121, 122 etc.) is taken from the base of the column and recycled to reactor 404. Stream 408, containing HF and (mainly) HCFC 123 is taken as a sidestream from the middle of column 406, combined with stream 422 containing HCFC 224 recycle and, optionally, stream 410 providing HF feed; the combined stream 411 is fed as a gas to hydrofluorination reactor 412 containing chromia catalyst. The product gas from this reactor, stream 413 is fed to distillation column 406 as described above. A lights stream 409 containing product HFA 125, HCFC 124, CFCs 114 and 114a, HCl and some HF is taken from the top of column 406, fed to an aqueous scrubbing system 414 in which HF and HCl are separated as an aqueous stream 415 from an organics stream 416. The organics stream 416 is dried, compressed in compressor 417 and fed to distillation column 418 in which a HFA 125 stream 419 is separated from stream 420 containing HCFC 124 and CFCs 114/114a. Stream 420 is fed to distillation column 421 in which a HCFC 124 stream 422 is separated from stream 423, enriched in CFCs114/114a.

Figure 5:
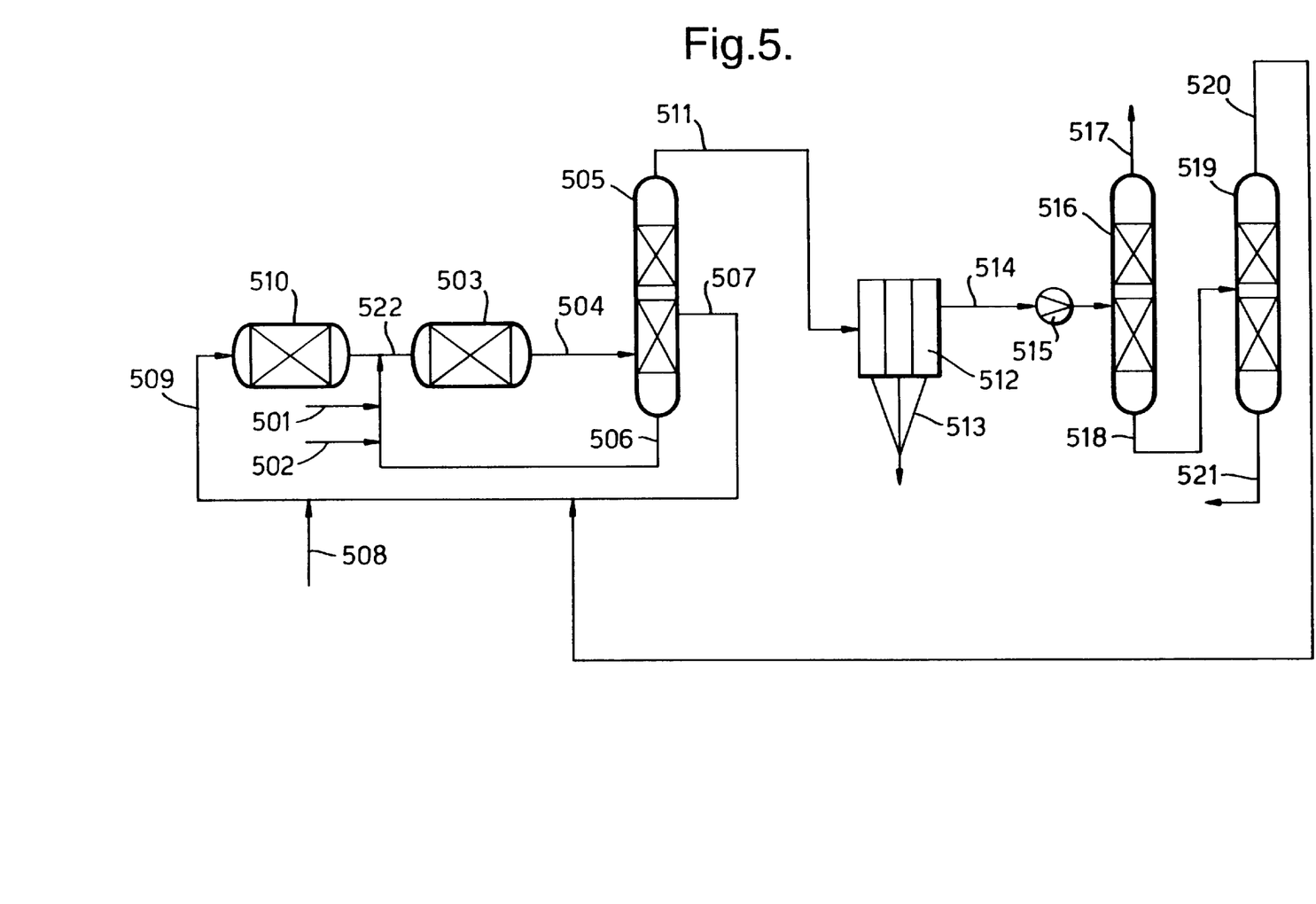
FIG. 5 is a schematic flow diagram of an embodiment of the invention using two reactors in which step (i) is the hydrofluorination of perchloroethylene and the reactors are arranged in series.

In the embodiment of FIG. 5, a gaseous stream 522 comprising feed hydrogen fluoride 501, feed perchloroethylene 502, recycled HF, perchloroethylene and underfluorinated intermediates to HFA-125 506, and product gas from hydrofluorination reactor 510 is fed to hydrofluorination reactor 503 containing chromia catalyst. The product gas 504 is fed to a distillation column 505 in which a stream 506 containing HF and perchloroethylene (and some underfluorinated HCFCs 121, 122 etc.) is taken from the base of the column and recycled to reactor 503, stream 507 containing HF and (mainly) HCFC-123 is removed as a side stream and combined with stream 520 containing recycled HCFC 124 and, optionally, stream 508 providing HF feed; the combined stream 509, is fed as a gas to hydrofluorination reactor 510 containing chromia catalyst. From the top of distillation column 505 is taken stream 511 containing light organics—product HFA 125, HCFC 124, CFCs 114, 114a etc., HCl and HF. The HCl and HF content of this stream is separated as an aqueous acid stream 513 in aqueous scrubbing system 512, while the organics stream 514 is dried, compressed in compressor 515 and fed to distillation column 516 in which a HFA 125 stream 517 is separated from a HCFC 124/ CFCs 114/114a stream 518. Stream 518 is fed to a distillation column 519 in which HCFC 124 recycle stream 520, is separated from a bottoms stream 521 enriched in CFCs 114/114a.

Figure 6:
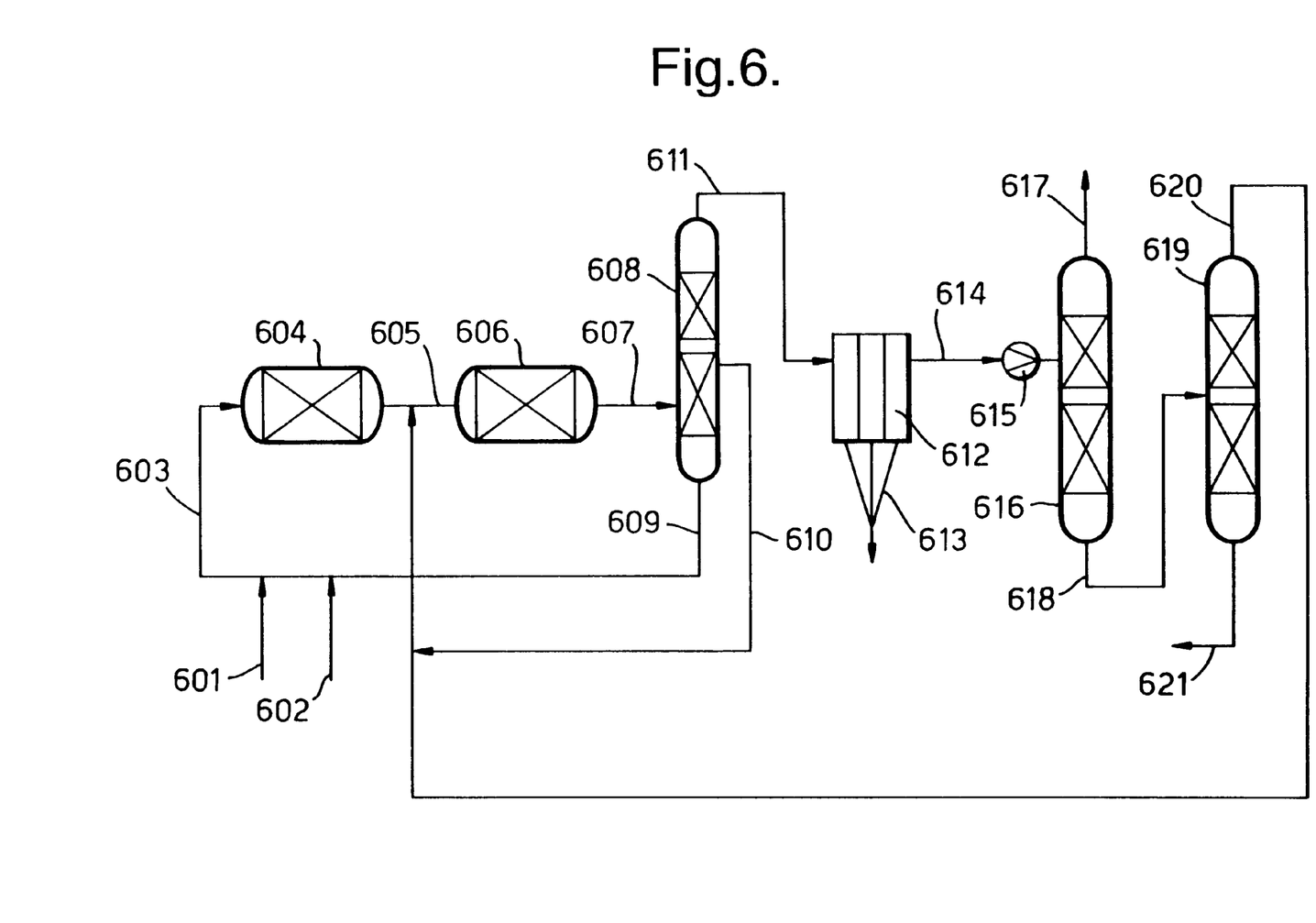
FIG. 6 is a schematic flow diagram of another embodiment of the invention using two reactors in which step (i) is the hydrofluorination of perchloroethylene and the reactors are arranged in series.

In the embodiment of FIG. 6, a gaseous stream 603 comprising feed HF 601, feed perchloroethylene 602, and recycled HF, perchloroethylene and underfluorinated intermediates to HFA 125 stream 609, is fed to a hydrofluorination reactor 604 containing chromia catalyst. The product gas stream 605 is mixed with a combined recycle stream 620 containing HF and (mainly) HCFC 123 and a HCFC 124 recycle stream 620 to give gaseous strewn 605. This is fed to a separate hydrofluorination reactor 606, also containing chromia catalyst. The product gas 607 is fed to a distillation column 608 in which a stream 609 containing HF, perchloroethylene (and some underfluorinated HCFCs 121, 122) is taken from the base of the column for recycle to reactor 604; stream 610 comprising HF and mainly HCFC-123 is taken as a sidestream, combined with recycle stream 620 and returned to reactor 606; and a lights stream 611 containing product HFA 125, HCFC 124, CFCs 114, 114a, HCl and some HF is fed to an aqueous scrubbing system 612. In 612 hydrogen chloride and HF are separated as an aqueous stream 613 from the organics 614. The organics stream 614 is dried, compressed in compressor 615 and fed to distillation column 616 in which a HFA 125 stream 617 is separated from stream 618 containing HCFC 124 and CFCs 114/114a. Stream 618 is fed to distillation column 619 in which a HCFC 124 stream 620 is separated from a stream 621 enriched in CFCs 114/114a.

Figure 7:
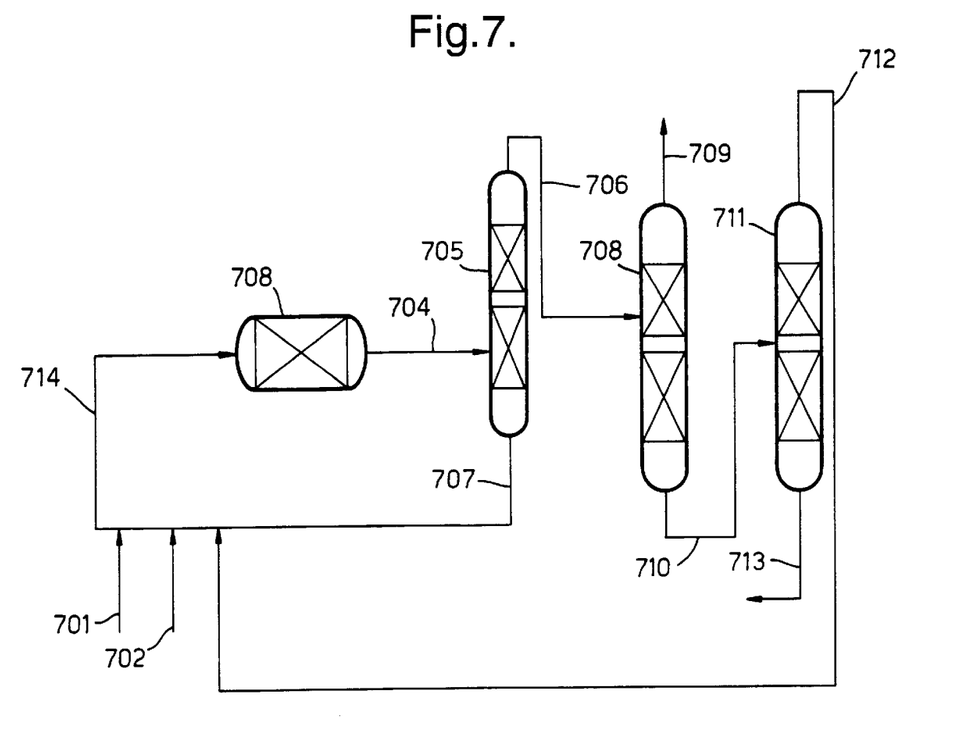
FIG. 7 is a schematic flow diagram of an embodiment of the invention in which step (i) is the hydrofluorination of perchloroethylene and steps (i) and (iii) are effected in a single reactor.

In the embodiment of FIG. 7, a gaseous feed stream 714, comprising a feed hydrogen fluoride stream 701, perchloroethylene stream 702, recycled HF/organics stream 707, and a hydrogen fluoride/tetrafluorochloroethane recycle stream 712 is fed to a hydrofluorination reactor 703, containing chromia catalyst. The product gas stream 704 is fed to a distillation column 705 in which a stream 707 containing unreacted hydrogen fluoride, perchloroethylene, and underfluorinated organic intermediates e.g. HCFCs 121,122, 123 and 1111 is separated from a stream 706 comprising product HFA 125, HCFC 124, CFCs 114/114a, HCFC 133a, HCl and HF. Stream 706 is fed to distillation column 708 in which stream 709 containing HCl, product HFA 125, and low levels of HF, is removed as an overhead stream for final product work up [e.g. aqueous scrubbing, drying, compression and distillation], while tetrafluorochloroethane, HF, CFC 114a, CFC 114 and HCFC 133a are removed as bottoms stream 710. This stream is fed to distillation column 711 in which stream 712 containing HF and tetrafluorochloroethane is removed as an overheads stream and recycled to reactor 703, while stream 713 enriched in CFC 114/114a is removed from the base of the column.

The invention is further illustrated but not limited by the following examples.

EXAMPLE 1

Hydrofluorination of Chlorotetrafluoroethane 2 g of a chromia catalyst of particle size 1 mm was charged to a ¼" internal diameter Inconel reactor tube and the catalyst was pre-fluorinated by passing hydrogen fluoride over the catalyst with a flow rate of 20 mls/minute at 300° C. for 24 hours. 8 mls/minute of chlorotetrafluoroethane were then added to the hydrogen fluoride feed and the mixture passed over the catalyst. The reactor off-gas was sampled at various temperatures and the samples were analysed by Gas Chromatography. The results are shown in Table 1.

TABLE 1

| Temperature. (° C.) | 125 Yield. (%) |
| --- | --- |
| 300 | 14.2 |
| 310 | 16.1 |
| 320 | 36.2 |

Chloropentafluoroethane was not observed in the product gases, and this example illustrates that the production of chloropentafluoroethane is eliminated where the presence of CFCs 114/114a are not present in the HCFC 124 starting material.

EXAMPLE 2

Chromia catalyst (1 g) was charged to an Inconel reactor (¼" diameter). HF (60 ml/min) was passed over the catalyst at 340° C. for 16 hours. Flows of Chlorine and HCFC 133a were introduced at the rates specified bellow. The offgas composition from the reactor was monitored by GC and the results observed are given below in Table 2.

TABLE 2

| Gas Flow (ml/min) | | | Offgas Composition (GC Area %) | | | | |
|---|---|---|---|---|---|---|---|
| HF | Cl$_2$ | HCFC133a | 133a | 134a | 123 | 124 | 113 |
| 60 | 0.92 | 27 | 84.8 | 11.0 | 2.2 | 1.3 | 0.06 |
| 60 | 0.48 | 27 | 86.6 | 10.9 | 1.3 | 0.6 | 0.02 |
| 60 | 0.24 | 27 | 87.8 | 10.6 | 0.8 | 0.4 | 0.00 |

EXAMPLE 3

Purification of HCFC 124 from Mixtures Containing 124, 114 and 114a

This example demonstrates the ease of separating CFCs 114/114a from HCFC 124 by distillation, when compared with separating CFC 115 from HFA 125.

In this example, all compositions are quoted as mol %.

A still comprising a 250 ml flask, a 5 theoretical stage vacuum jacketed packed column [packed with Raschig rings], condenser and take-off controller was charged with 150 g of a mixture of 90 mol % 124, 4.5 mol % 114/114a and 5.5 mol % 133a. The column was stabilised at approximately –12 C under total reflux at atmospheric pressure. Following equilibration, a vapour sample was removed from the column top and was shown by GC analysis to have the composition:

124—99.4
133a—0.15
114/114a—0.08

Distillation continued at a reflux ratio of 5:1 until approximately half of the initial charge had been distilled. A sample of the vapour in the top of the column was removed and analysed by GC as HCFC 124—99.98
CFCs 114/114a—n/d
HCFC 133a—n/d

COMPARATIVE EXAMPLE 1

Example 3 was repeated using the same apparatus as described above, 150 g of a mixture of HFA 125—98.2% and CFC 115—1.8%. After equilibration under total reflux at approximately –50 C, a vapour sample was taken and analysed as:

HFA 125—98.0 CFC 115—2.0

After distillation of about half the charge at a reflux ratio of 5:1, the distillate composition was:

HFA 125—99.3 CFC 115—1.7

We claim:

1. A process for the production of pentafluoroethane which comprises the steps (i) producing a composition comprising a compound of formula C$_2$HCl$_x$F$_y$ in which x=1, 2 or 3 and y=2, 3 or 4 provided that x+y is 5, contaminated with a compound of formula C$_2$Cl$_{x+1}$F$_y$, (ii) separating the compound of formula C$_2$HCl$_x$F$_y$ from the compound of formula C$_2$Cl$_{x+1}$F$_y$ and (iii) contacting the compound of formula C$_2$HCl$_x$F$_y$ with hydrogen fluoride in the presence of a fluorination catalyst whereby to produce pentafluoroethane.

2. A process as claimed in claim 1 in which steps (i), (ii) and (iii) are effected in that order.

3. A process as claimed in claim 1 which further comprises treating the product stream from step (iii) to separate unconverted compounds of formula C$_2$HCl$_x$F$_y$ from pentafluoroethane and recycling unconverted compounds of formula C$_2$HCl$_x$F$_y$ to step (i) or step (iii).

4. A process as claimed in claim 3 wherein the recycle stream comprises less than 15 wt % of compounds of formula C$_2$Cl$_{x+1}$F$_y$ based on the total weight of compounds of formula C$_2$HCl$_x$F$_y$ and C$_2$Cl$_{x+1}$F$_y$ present in the recycle stream.

5. A process as claimed in claim 1 in which the compound of formula C$_2$HCl$_x$F$_y$ is chlorotetrafluoroethane and the compound of formula C$_2$Cl$_{x+1}$F$_y$ is dichlorotetrafluoroethane.

6. A process as claimed in claim 1 in which the level of chloropentafluoroethane produced is less than 2 wt % based upon the amount of compound of formula C$_2$HCl$_x$F$_y$ fed to step (iii).

7. A process as claimed in claim 1 in which in step (ii) at least 50 wt % of the compounds of formula C$_2$Cl$_{x+1}$F$_y$ present in the composition produced in step (i) are separated from the compounds of formula C$_2$HCl$_x$F$_y$.

8. A process as claimed in claim 7 in which at least 75 wt % of the compounds of formula C$_2$Cl$_{x+1}$F$_y$ present in the composition produced in step (i) are separated from the compounds of formula C$_2$HCl$_x$F$_y$.

9. A process as claimed in claim 1 in which step (ii) comprises distilling the composition.

10. A process as claimed in claim 1 in which the composition produced in step (i) comprises from about 0.1% to about 20% by weight of compounds of formula C$_2$Cl$_{x+1}$F$_y$ based on the total weight of compounds of formula C$_2$HCl$_x$F$_y$ and C$_2$Cl$_{x+1}$F$_y$ present in the composition.

11. A process as claimed in claim 10 in which the composition comprising the compound of formula C$_2$HCl$_x$F$_y$ fed to step (iii) contains less than 10 wt % of compounds of formula C$_2$Cl$_{x+1}$F$_y$ based on the total weight of compounds of formula C$_2$HCl$_x$F$_y$ and C$_2$Cl$_{x+1}$F$_y$ present in the composition.

12. A process as claimed in claim 11 in which the composition comprising the compound of formula C$_2$HCl$_x$F$_y$ fed to step (iii) contains less than 2 wt % of compounds of formula C$_2$Cl$_{x+1}$F$_y$ based on the total weight of compounds of formula C$_2$HCl$_x$F$_y$ and C$_2$Cl$_{x+1}$F$_y$ present in the composition.

13. A process as claimed claim 1 in which step (iii) is effected in the vapour phase at elevated temperature.

14. A process as claimed in claim 13 in which the temperature is in the range from about 200° C. to about 500° C.

15. A process as claimed in claim 13 in which in step (iii) the fluorination catalyst comprises chromia, chromium oxyfluoride, alumina or aluminium oxyfluoride.

16. A process as claimed in claim 15 in which in step (iii) the fluorination catalyst comprises one or more metals and chromia, chromium oxyfluoride, alumina or aluminium oxyfluoride.

17. A process as claimed in claim 16 in which in step (iii) the fluorination catalyst comprises an activity promoting amount of zinc and chromia, chromium oxyfluoride, alumina or aluminium oxyfluoride.

18. A process as claimed in claim 1 in which step (i) comprises chlorinating trichloroethylene or a compound of formula C$_2$H$_2$X$_4$ in which X is fluorine or chlorine.

* * * * *